United States Patent [19]
Gaster et al.

[11] Patent Number: 6,159,979
[45] Date of Patent: Dec. 12, 2000

[54] BICYCLIC ARYL OR A BICYCLIC HETEROCYCLIC RING CONTAINING COMPOUNDS HAVING A COMBINED $5HT_{1A}$, $5HT_{1B}$ AND $5HT_{1D}$ RECEPTOR ANTAGONISTIC ACTIVITY

[75] Inventors: Laramie Mary Gaster, Bishop's Stortford; Paul Adrian Wyman, Epping, both of United Kingdom

[73] Assignee: SmithKline Beecham p.l.c., Brentford, United Kingdom

[21] Appl. No.: 09/403,149

[22] PCT Filed: Apr. 14, 1998

[86] PCT No.: PCT/EP98/02265

§ 371 Date: Oct. 15, 1999

§ 102(e) Date: Oct. 15, 1999

[87] PCT Pub. No.: WO98/47885

PCT Pub. Date: Oct. 29, 1998

[30] Foreign Application Priority Data

Apr. 18, 1997 [GB] United Kingdom .................... 9707876
Jan. 26, 1998 [GB] United Kingdom .................... 9801635

[51] Int. Cl.[7] ...................... A61K 31/495; C07D 241/00; C07D 401/00
[52] U.S. Cl. ................................ 514/252.12; 514/252.13; 544/358; 544/360; 544/361; 544/392; 544/399; 544/400

[58] Field of Search ...................................... 514/249, 250, 514/252.12, 252.13; 544/358, 360, 361, 392, 399, 400

[56] References Cited

U.S. PATENT DOCUMENTS 5,556,969  9/1996  Chambers et al. ...................... 540/509

FOREIGN PATENT DOCUMENTS

| 2 276 165 | 9/1994 | United Kingdom . |
| WO 95/04729 | 2/1995 | WIPO . |
| WO 95/06044 | 3/1995 | WIPO . |
| WO 96/02525 | 2/1996 | WIPO . |
| 9827058 | 8/1997 | WIPO . |
| WO 97/28141 | 8/1997 | WIPO . |

OTHER PUBLICATIONS

C. Jorand–Lebrun, et al., "Arylpiperazide Derivatives of Phenylpiperazines as a New Class of Potent and Selective $5-HT_{1B}$ Receptor Antagonists", (1997), Bioorganic & Medicinal Chemistry Letters, vol. 7, No. 24, pp. 3183–3188.

*Primary Examiner*—Mukund J. Shah
*Assistant Examiner*—Sudhaker B. Patel
*Attorney, Agent, or Firm*—Soma G. Simon; William T. King; Charles M. Kinzig

[57] ABSTRACT

Novel bicyclic aryl/bicyclic heterocyclic ring containing compounds having a combined $5HT_{1A}$, $5HT_{1B}$ and $5HT_{1D}$ receptor antagonistic activity are provided.

13 Claims, No Drawings

BICYCLIC ARYL OR A BICYCLIC HETEROCYCLIC RING CONTAINING COMPOUNDS HAVING A COMBINED $5HT_{1A}$, $5HT_{1B}$ AND $5HT_{1D}$ RECEPTOR ANTAGONISTIC ACTIVITY

The present invention relates to novel piperazine derivatives, processes for their preparation, and pharmaceutical compositions containing them.

WO 95/06637, WO 95/06044 and WO 95/04729 disclose a series of piperazine derivatives which are said to possess $5HT_{1D}$ receptor antagonist activity. These compounds are alleged to be of use in the treatment of various CNS disorders such as depression with the advantage of a relatively fast onset of action. EPA 0533266/7/8 disclose a series of benzanilide derivatives which are said to possess $5-HT_{1D}$ receptor antagonist activity.

A structurally distinct class of compounds have now been found to exhibit combined $5HT_{1A}$, $5HT_{1B}$ and $5HT_{1D}$ receptor antagonist activity. It is expected that such compounds will be useful for the treatment and prophylaxis of various CNS disorders. In a first aspect, the present invention therefore provides a compound of formula (I) or a salt thereof:

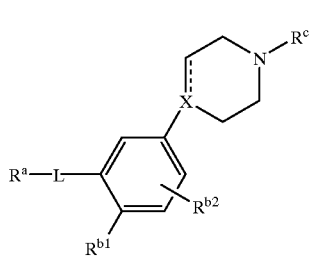

(I)

in which $R^a$ is a group of formula (i)

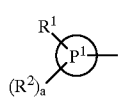

(i)

in which $P^1$ is bicyclic aryl, or a bicyclic heterocyclic ring containing 1 to 3 heteroatoms selected from oxygen, nitrogen and sulphur; $R^1$ is hydrogen, halogen, $C_{1-6}$alkyl, $C_{3-6}$cycloalkyl, $COC_{1-6}$alkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, $C_{1-6}$alkanoyl, nitro, trifluoromethyl, cyano, $SR^9$, $SOR^9$, $SO_2R^9$, $SO_2NR^{10}R^{11}$, $CO_2R^{10}$, $CONR^{10}R^{11}$, $CO_2NR^{10}R^{11}$, $CONR^{10}(CH_2)_cCO_2R^{11}$, $(CH_2)_cNR^{10}R^{11}$, $(CH_2)_cCONR^{10}R^{11}$, $(CH_2)_cNR^{10}COR^{11}$, $(CH_2)_cCO_2C_{1-6}$alkyl, $CO_2(CH_2)_cOR^{10}$, $NR^{10}R^{11}$, $NR^{10}CO_2R^{11}$, $NR^{10}CONR^{10}R^{11}$, $CR^{10}=NOR^{11}$, $CNR^{10}=NOR^{11}$, where $R^9$, $R^{10}$ and $R^{11}$ are independently hydrogen or $C_{1-6}$alkyl and c is 1 to 4; $R^2$ is hydrogen, halogen, $C_{1-6}$alkyl, $C_{3-6}$cycloalkyl, $C_{3-6}$cycloalkenyl, $C_{1-6}$alkoxy, $C_{1-6}$alkanoyl, aryl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are as defined for $R^1$;
a is 1, 2 or 3;

or $R^a$ is a group of formula (ii)

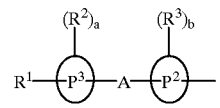

(ii)

wherein $P^2$ and $P^3$ are independently phenyl, bicyclic aryl, a 5- to 7- membered heterocyclic ring containing 1 to 3 heteroatoms selected from oxygen, nitrogen and sulphur, or a bicyclic heterocyclic group containing 1 to 3 heteroatoms selected from oxygen, nitrogen or sulphur, providing that at least one of $P^2$ and $P^3$ is a bicyclic aryl or bicyclic heterocyclic group;
A is a bond or oxygen, $S(O)_m$ where m is 0 to 2, carbonyl, $CH_2$ or $NR^4$ where $R^4$ is hydrogen or $C_{1-6}$alkyl;
$R^1$ is as defined above for forrnula (i) or is a 5 to 7-membered heterocyclic ring, containing 1 to 3 heteroatoms selected from oxygen, nitrogen or sulphur, optionally substituted by $C_{1-6}$alkyl, halogen or $C_{1-6}$ alkanoyl;
$R^2$ and $R^3$ are independently hydrogen, halogen, $C_{1-6}$alkyl, $C_{3-6}$cycloalkyl, $C_{3-6}$cycloalkenyl, $C_{1-6}$alkoxy, $C_{1-6}$alkanoyl, aryl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are as defined for $R^1$; and a and b are independently 1, 2 or 3;
L is a group of formula

—C(=V)—DG— or

—DG—C(=V)— or

—Y—C(=V)—DG$^1$—

V is oxygen or sulphur;
D is nitrogen, carbon or a CH group, G and $G^1$ are each hydrogen or $C_{1-6}$alkyl, providing that D is nitrogen or a CH group, or G together with $R^{b1}$ forms a group W where W is $(CR^{16}R^{17})_t$ where t is 2, 3 or 4 and $R^{16}$ and $R^{17}$ are independently hydrogen or $C_{1-6}$alkyl or W is $(CR^{16}R^{17})_u$-J where u is 0, 1, 2 or 3 and J is oxygen, sulphur, $CR^{16}$=$CR^{17}$, $CR^{16}$=N, =$CR^{16}$O,=$CR^{16}$S or=$CR^{16}$—$NR^{17}$;
Y is —NH— or —$NR^5$— where R5 is $C_{1-6}$ alkyl,or Y is —$CH2$— or—O—:
X is nitrogen or carbon;
$R^{b1}$ and $R^{b2}$ are independently hydrogen, halogen, hydroxy, $C_{1-6}$alkyl, trifluoromethyl, $C_{1-6}$alkoxy or aryl, or $R^{b1}$ together with G forms a group W as defined above;
$R^c$ is hydrogen or $C_{1-6}$alkyl; and
—is a single bond when X is nitrogen, or a single or double bond when X is carbon.

$C_{1-6}$alkyl groups whether alone or as part of another group may be straight chain or branched. The term 'acyloxy' is used herein to describe a group—$OC(O)C_{1-6}$alkyl. The term 'aryl' is used herein to describe, unless otherwise stated, a group such as phenyl. The term 'aralkyl' is used herein to describe, unless otherwise stated, a group such as benzyl.

The bicyclic aryl group represented by $P^1$, $P^2$ and/or $P^3$, which may be partially saturated, is preferably naphthyl. When the bicyclic aryl group is partially saturated suitable examples include indanyl and tetrahydronaphthyl.

The bicyclic heterocyclic rings represented by $P^1$, $P^2$ and/or $P^3$ may be partially saturated, such as 2,3-dihydrobenzofuryl. Examples of bicyclic heterocyclic rings include quinoline, isoquinoline, indole, benzofuran, benzothiazole and benzothiadiazole. The heterocyclic groups can be linked to the remainder of the molecule via a carbon atom or, when present, a suitable nitrogen atom.

Examples of 5 to 7 membered heterocyclic rings containing 1 to 3 heteroatoms selected from oxygen, nitrogen and sulphur represented by $P^1$, $P^2$ and/or $P^3$, include thienyl, furyl, pyrrolyl, triazolyl, imidazolyl, oxazolyl, thiazolyl, oxadiazolyl, isothiazolyl, isoxazolyl, thiadiazolyl, pyrimidyl and pyrazinyl, preferably pyridyl.

$R^1$ is preferably a halogen atom for example, fluorine, chlorine or bromine or a, and $R^2$ and/or $R^3$ are each preferably hydrogen, halogen for example a chloro group, a $C_{1-6}$alkyl group for example a methyl group or a $C_{1-6}$anoyl group such as acetyl.

a and b are each preferably 1 or 2.

A is preferably a bond or oxygen.

In the group L, as defined above:

V is preferably oxygen.

D is preferably nitrogen and G is preferably a hydrogen atom or together with $R^{b1}$ forms group W, preferably —$(CH_2)_2$—.

$R^{b1}$ and $R^{b2}$ are preferably hydrogen or a halogen atom for example chlorine, or a $C_{1-6}$alkoxy group for example methoxy, or $R^{b1}$ together with G forms W referred to above.

$R^c$ is preferably a $C_{1-6}$alkyl group for example methyl.

X is preferably a nitrogen atom.

Preferably the group $R^{b2}$ has a para relationship with respect to the group $R^aL$.

Particularly preferred compounds according to the invention include:
N-[4-methoxy-3-(4-methylpiperazin-1-yl)phenyl]-4-bromonaphth-1-yl carboxamide, 5-bromo-N-[4-methoxy-3-(4-methylpiperazin-1-yl)phenyl]naphth-1-yl carboxamide, N-[4-methoxy-3-(4-methylpiperazin-1-yl)phenyl]quinolin-4-yl carboxamide, N-[4-methoxy-3-(4-methylpiperazin-1-yl)phenyl]-5-(pyridin-4-yl)naphth-1-yl carboxamide, N-[4-methoxy-3-(4-methylpiperazin-1-yl)phenyl]-4-(pyridin-4-yl)naphth-1-yl carboxamide, N-[(4-methoxy-3-(4-methylpiperazin-1-yl)phenyl]-N'-[naphth-1-yl]urea, N-[4-bromonaphth-1-yl]-N'-[(4-methoxy-3-(4-methylpiperazin-1-yl)phenyl]urea, N-[4-methoxy-3-(4-methylpiperazin-1-yl)phenyl]-N'-[4-(pyridin-4-yl)naphth-1 -yl]urea, N-[4-methoxy-3-(4-methylpiperizin-1-yl)phenyl]-4-bromonaphth-1 -yl acetamide, N-[4-methoxy-3-(4-methylpiperazin-1-yl)phenyl]-4-(pyridin-4-yl)naphth-1 -yl acetamide, N-[4-chloro-3-(4-methylpiperazin-1-yl)phenyl]-N'-[4-(pyridin-4-yl)naphth-1-yl]urea, N-[4-methoxy-3-(4-methylpiperazin-1-yl)phenyl]-N'-[naphth-1-yl]thiourea, N-[4-methoxy-3-(1-methylpiperidin-4-yl)phenyl]-N'-[4-(pyridin-4-yl)naphth-1-yl]urea, N-[4-methoxy-3-(4-methylpiperazin-1-yl)phenyl]-N'-[5,6,7,8-tetrahydronaphth-1-yl]urea, N-[Indian-5-yl]-N'-[4-methoxy-3-(4-methylpiperazin-1-yl)phenyl]urea, N-[benzo-2,1,3-thiadiazol-4-yl]-N'-[4-methoxy-3-(4-methylpiperazin-1-yl) phenyl]urea, N-[indol-4-yl]-N'-[4-methoxy-3-(4-methylpiperazin-1-yl)phenyl]urea, N-[4-methoxy-3-(4-methylpiperazin-1-yl)phenyl]-N'-[3,4-methylenedioxyphenyl]urea, N-[5-Bromonaphth-1-yl]-N'-[4-methoxy-3-(4-methylpiperazin-1-yl)phenyl]urea, 5-Bromo-N-[4-methoxy-3-(4-methylpiperazin-1-yl)phenyl] naphth-1-ylacetarnide, N-[4-Methoxy-3-(4-methylpiperazin-1-yl)phenyl]-N'-[2-methylquinolin-6-yl]urea, N-[Isoquinolin-5-yl]-N'-[4-methoxy-3-(4-methylpiperazin-1-yl)phenyl]urea, N-[Benzothiazol-6-yl]-N'-[4-methoxy-3-(4-methylpiperazin-1-yl)phenyl]urea, N-[4-Methoxy-3-(4-methylpiperazin-1-yl)phenyl]-N-[quinolin-3-yl]urea, N-[4-Methoxy-3-(4-methylpiperazin-1-yl)phenyl]-N'-[quinolin-6-yl]urea, N-[4-Methoxy-3-(4-methylpiperazin-1-yl)phenyl]-N'-[quinolin-5-yl]urea, N-[2,3-Dihydrobenzofuran-5-yl]-N'-[4-methoxy-3-(4-methylpiperazin-1-yl)phenyl]urea N-[4-Methoxy-3-(4-methylpiperazin-1-yl)phenyl]-4-(pyridin-3-yl)naphth-1-ylacetamide, N-[4-Methoxy-3-(4-methylpiperazin-1-yl) phenyl]-N'-[5-(pyridin-3-yl)naphth-1yl]urea, 4-(4-Acetylphenyl)-N-[4-methoxy-3-(4-methylpiperazin-1-yl) phenyl]naphth-1-ylacetarnide, 4-(3-Acetylphenyl)-N-[4-methoxy-3-(4-methylpiperazin-1-yl)phenyl]naphth-1-ylacetamide, 5-(3-Acetylphenyl)-N-[4-methoxy-3-(4-methylpiperazin-1-yl)phenyl]naphth-1-ylacetarnide, N-[4-Methoxy-3-(4-methylpiperazin-1-yl)phenyl]-N'-[5-phenylnaphth-1-yl]urea, N-[4-Methoxy-3-(4-methylpiperazin-1-yl)phenyl]-5-(pyridin-3-yl)naphth-1-ylacetamide, N-[4-Methoxy-3-(4-methylpiperazin-1-yl) phenyl]-5-phenylnaphth-1-ylacetamide, 5-(4-Acetylphenyl)-N-[4-methoxy-3-(4-methylpiperazin-1-yl) phenyl]naphth-1-ylacetamide, N-[4-Methoxy-3-(4-methylpiperazin-1-yl)phenyl]-5-(2-methylphenyl)naphth-1-ylacetamide, N-[4-Bromo-3-(4-methylpiperazin-1-yl) phenyl]-4-(pyridin-4-yl)naphth-1-ylacetamide, 5-(3,4-Dimethoxyphenyl)-N-[4-methoxy-3-(4-methylpiperazin-1-yl)phenyl]naphth-1-ylacetamide, N-[5-(3-Acetylphenyl) naphth-1-yl]-N'-[4-methoxy-3-(4-methylpiperazin-1-yl) phenyl]urea, N-[4-Chloro-3-(1-methylpiperidin-4-yl) phenyl]-4-(pyridin-4-yl)naphth-1-ylacetamide, 5-Bromo-6-(4-methylpiperazin-1-yl)-1-[5-(pyridin-4-yl)naphth-1ylcarbonyl]-1H-indole or pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Compounds of the invention can be prepared using procedures known in the art. In a further aspect the present invention provides a process for the preparation of a compound of formula (I) which comprises (a) where L is —C(=V)—DG— or —DG—C(=V)—, coupling a compound of formula (II):

$$Ra—L^1 \qquad (II)$$

with a compound of formula (III).

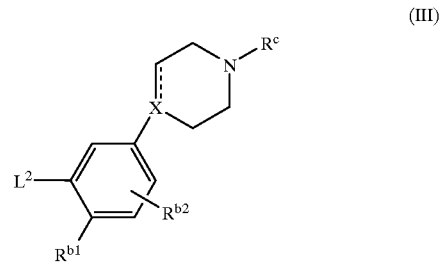

(III)

in which $R^a, R^{b1}, R^{b2}, R^c$ and X are as defined in formula (I) and $L^1$ and $L^2$ contain the appropriate functional groups which are capable of reacting together to form the L moiety; or (b) where L is —Y—C(=V)—$DG^1$ in which D is nitrogen and Y is NH, coupling a compound of formula (IV):

 (IV)

in which $R^a$ and V are as defined in formula (I) or a protected derivative thereof with a compound of formula (V):

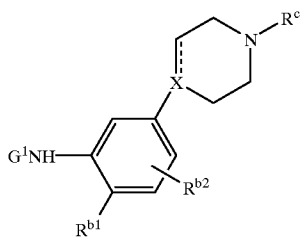 (V)

in which $R^{b1}, R^{b2}, R^c, G^1$ and X are as defined in formula (I), or a protected derivative thereof; or (c) where L is —Y—C(=V)—DG$^1$— in which D is nitrogen and and Y is NH or NR$^5$, reacting a compound of formula (VI)

 (VI)

in which $R^a$ and $R^5$ are as defined in formula (I) with a compound of formula (V) together with an appropriate urea forming agent;

(d) where L is —Y—C(=V)—DG$^1$— in which D is nitrogen and Y is CH$_2$ or O, reacting a compound of formula (VII)

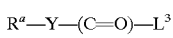 (VII)

in which $R^a$ is as defined in formula (I), and $L^3$ is an appropriate leaving group, with a compound of formula (V)

(e) where D is CH, reacting a compound of formula (VI)

 (VI)

in which $R^a$ is as defined in formula (I) with a compound of formula (VII)

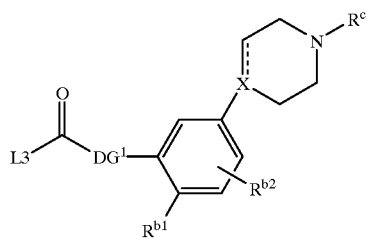 (VII)

in which D is CH, and $G^1$, X, $R^{b1}$, $R^{b2}$ and $R^c$ are as defined in formula (I) and $L^3$ is an appropriate leaving atom and optionally thereafter:

removing any protecting groups,
converting a compound of formula (I) into another compound of formula (I), forming a pharmaceutically acceptable salt.

In the reaction of the compounds of formulae (II) and (III), suitable examples of roups $L^1$ and $L^2$ include:

$L^1$ is COL$^a$ and $L^2$ is NH$_2$
$L^1$ is NH$_2$ and $L^2$ is COL$^a$
in which $L^a$ is an appropriate leaving group.

Suitably one of $L^1$ and $L^2$ is an activated carboxylic acid derivative such as an acyl chloride or acid anhydride, and the other is an amine group. Activated compounds of formulae (II) and (III) can also be prepared by reaction of the corresponding carboxylic acid with a coupling agent such as dicyclohexylcarbodiimide, carbonyldiimidazole or diphenylphosphorylazide. Preferably $L^1$ or $L^2$ is a group COLA where La is halo particularly chloro.

Compounds of formulae(II) and (III) are typically reacted together in an inert solvent such as dimethylformamide, tetrahydrofuran or dichloromethane at ambient or elevated temperature in the presence of a base such as an alkali metal hydroxide,triethylamine or pyridine.

The reaction in process (b) is conveniently effected in an organic solvent such as dichloromethane.

In process (c) the urea forming agent can be carbonyl diimidazole, triphosgene or phosgene, and carried out in an inert organic solvent such as dimethylformamide, tetrahydrofuran or dichloromethane at ambient or elevated temperature in the presence of a base such as triethylamine or pyridine.

In processes (d) and (e) the leaving group $L^3$ may be a halogen e.g. chloro group, and the reaction may be carried out in an inert organic solvent such as tetrahydrofuran or dichloromethane at ambient or elevated temperature in the presence of a base such as triethylamine or pyridine.

Compounds of formula (I) can be converted into further compounds of formula (I) using standard techniques. For example, in the case wherein $R_c$ is hydrogen, it is possible to introduce a $C_{1-6}$alkyl group by conventional alkylation using 1 molar equivalent of a $C_{1-6}$alkyl halide and 1 molar equivalent of a suitable base in an inert solvent.

Intermediate compounds of formula (II) and (III) can be prepared using standard procedures known in the art.

It will be appreciated to those skilled in the art that it may be necessary to protect certain reactive substituents during some of the above procedures. Standard protection and deprotection techniques can be used. For example, primary arnines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals, thioacetals or thioketals. Deprotection is achieved using standard conditions.

$5HT_{1A/1B/1D}$ receptor antagonists, and in particular the compounds of the present invention, are expected to be of use in the treatment of CNS disorders such as mood disorders, including depression, seasonal affective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; disorders of eating behaviours, including anorexia nervosa and bulimia nervosa: and sleep disorders. Other CNS disorders include motor disorders such as Parkinson's disease, dementia in Parkinson's disease, neuroleptic-induced Parkinsonism and tardive dyskinesias, as well as other psychiatric disorders.

$5HT_{1A/1B/1D}$ receptor antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction and hypothermia.

The present invention also provides a compound of general formula (I) or a physiologically acceptable salt or solvate thereof for use in the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Examples illustrate the preparation of compounds of the invention.

DESCRIPTION 1

4-(Pyridin-4-yl)naphth-1-ylamine

A stirred suspension of 4-bromonaphth-1-ylamine (10 g, 45 mnmole) in 1,2-dimethoxyethane (400 ml) and water (100 ml) containing sodium carbonate (14 g) was flushed with argon for 0.3h. Tetrakis (triphenylphosphine)palladium (0) (2.75 g, 2.4 mmole) was added followed by 4-pyridylboronic acid (5.7 g, 46 mmole) and the mixture heated at reflux for 5 h. The mixture was concentrated in vacuo to a brown slurry and partitioned between dichloromethane and water. The aqueous was further extracted with dichloromethane and the combined organics dried ($Na_2SO_4$) and concentrated in vacuo to a brown solid (13.2 g). Purification of the solid by flash chromatography eluting with ethyl acetate afforded the title compound as a yellow crystalline solid (7.8 g, 78%).

$^1$H NMR (250 MHz, $CDCl_3$) δ(ppm):8.68 (d, 2H), 7.90 (d, 2H), 7.30 (m, 5H), 6.84 (d, 1H), 4.32 (s, 2H).

DESCRIPTION 2

4-(Pyridin-4-yl)naphth-1-ylacetic Acid 4-Bromonaphth-1-ylacetic acid (1 g, 3.78 mmole, J. Org. Chem., 1951, 16, 1588) in 1,2-dimethoxyethane (50ml) was treated with 4-pyridylboronic acid (465mg, 3.78 mmole), sodium hydrogen carbonate (952 mg, 11.3 mmole) and water (10 ml). A stream of argon was bubbled through the mixture for 15 mins, then tetrakis (triphenylphosphine) palladium (0) (200mg 0.17 mmole) was added and the mixture heated under reflux for 18h. The mixture was then concentrated in vacuo to a gum, which was partitioned between 2N sodium hydroxide solution and dichloromethane. The aqueous layer was separated, adjusted to pH 0 with 6N hydrochloric acid and washed with dichloromethane;

then adjusted to pH 7 by addition of aqueous potassium carbonate solution and extracted with dichloromethane. The dichloromethane extract was dried ($Na_2SO_4$) and concentrated in vacuo to give the title compound, which crystallised from ether as needles mp 210–215° C. (465 mg, 46%).

$^1$H NMR (250 MHz, $CDCl_3$) δ(ppm): 8.55 (d, 2H), 8.0 (d, 1H), 7.7 (d, 1H), 7.5–7.3 (m, 5H), 7.2 (d, 1H), 6.1 (br s, 1H), 4.0 (s, 2H).

DESCRIPTION 3

2,3-Dihydrobenzofuran-5-yl Isocyanate

To a stirred suspension of 2,3-dihydobenzofuran-5-carboxylic acid (1.0 g, 6.1 mmol) in $CH_2$ $Cl_2$ (30 ml) was added oxalyl chloride (1.55 g, 12.2 mmol) dropwise over 2 minutes followed by dimethylformamide (1 drop). After 20 hours the solvent and excess oxalyl chloride were removed in vacuo giving the acid chloride as a yellow solid. This was dissolved in $CH_2$ $Cl_2$ (60 ml) and cooled in an ice bath with stirring. Tetrabutylammonium iodide (0.032 g) was added, followed by a solution of sodium azide (0.555 g, 8.5 mmol) in $H_2O$ (12 ml). After 3 hours of vigorous stirring at approx. 0° C., water (45 ml) was added and the $CH_2$ $Cl_2$ layer separated, dried ($Na_2SO_4$) and concentrated carefully in vacuo to afford the acyl azide. This was dissolved in toluene (50 ml) and heated under reflux for 2 hours, then concentrated in vacuo to afford the title compound as a yellow/brown solid (0.98 g, 100%).

¹H NMR (250 MHz, CDCl₃) δ(ppm): 6.92 (d,1H), 6.83 (dd, 1H), 6.68 (d, 1H), 4.58 (t, 2H), 3.19 (t, 2H).

DESCRIPTION 4
5-Bromonaphth-1-yl Isocyanate

To a stirred suspension of 1-naphthoic acid (90 g, 0.52 mol) in glacial acetic acid at 100° C. was added bromine (84 g, 0.52 mol). The reaction was stirred at this temperature for 1.5 hours and then allowed to cool overnight. The resulting slurry was diluted with glacial acetic acid, the solid collected by filtration, resuspended in water, filtered and dried in vacuo to give 5-bromo-1-napthoic acid (100 g). The acid was converted to the title compound using a similar procedure to Description 3 (68%).

¹H NMR (250 MHz, CDCl₃) δ(ppm): 8.15 (t, 2H), 7.85 (d, 1H), 7.3–7.65 (m, 3H).

DESCRIPTION 5
1-Methyl-4-(3-nitrophenyl)pyridinium Iiodide

A suspension of 1-bromo-3-nitrobenzene (9.0 g, 44.5 mmol) and Na₂CO₃ (14 g) in dimethoxyethane (160 ml) and water (40 ml) was bubbled through with argon for 15 mins. To the mixture was added 4-pyridylboronic acid (5.5 g, 44.7 mmnol) and tetrakis(triphenylphosphine)palladium (0) (2.5 g, 2.1 mmol) and the mixture heated at reflux for 18 h. On cooling the solvent was removed in vacuo and the crude product extracted with dichloromethane, dried (Na₂SO₄) and evaporated in vacuo to a brown solid. This was dissolved in dichloromethane (100 ml), treated with methyl iodide (5.5 ml, 88.0 mmol) and left to stand for 24h. The resultant precipitate was filtered and dried in vacuo to give the title compound as a yellow crystalline solid (4.35 g, 29%).

¹H NMR (250 MHz, d⁶DMSO) δ(ppm): 9.15 (d, 2H), 8.88 (s, 1H), 8.70 (d, 2H), 8.53 (t, 2H), 7.98 (t, 1H), 4.41 (s, 3H).

DESCRIPTION 6
3-(1-Methylpiperidin-4-yl)aniline

To a solution of 1-methyl-4-(3-nitrophenyl)pyridinium iodide (D5, 4.0 g, 11.7 mmol) in ethanol (100 ml) and water (100 ml) at 0° C. was added sodium borohydride (665 mg, 17.6 mmol) portionwise over 0.5 h, before allowing to warm to room temperature while stirring for 2h. To the mixture was added 10% NaOH solution (100 ml) and the product extracted with dichloromethane (2×), dried (Na₂SO₄) and evaporated in vacuo to a brown oil (2.6 g). The oil was dissolved in ethanol (100 ml) and hydrogenated over 10% Pd—C at 50 psi and 50° C. for 48 h. Filtration and evaporation in vacuo of the filtrate gave the title compound as a yellow oil (2.1 g, 93%).

¹H NMR (250 MHz, d⁶DMSO) δ(ppm): 6.94 (t, 1H), 6.41 (m, 3H), 4.96 (br s, 2H), 3.47 (m, 2H), 2.87 (m, 2H), 2.21 (s, 3H), 1.96 (m, 2H), 1.62 (m, 3H).

DESCRIPTION 7
4-Chloro-3-(1-methylpiperidin-4-yl)aniline

To a solution of 3-(1-methylpiperidin-4-yl)aniline (D6, 1.0 g, 5.3 mmol) in dichloromethane (50 ml) containing triethylarnine (1.1 ml, 7.9 mmol) was added dropwise acetyl chloride (0.40 ml, 5.6 mmol) and the mixture stirred at room temperature overnight. The mixture was washed with aqueous 10% sodium carbonate and the organics dried (Na₂SO₄), and evaporated in vacuo to a red semi-solid (1.49 g). To a solution of the solid in 1,2-dichloroethane (100 ml) was added N-chlorosuccinimide (1.2 g, 9.0 mmol) and the mixture heated at 80° C. for 28 h. On cooling, water (50 ml) was added and the aqueous basified with aqueous 10% sodium carbonate. The aqueous was extracted with dichloromethane (3×), the combined organics dried (Na₂SO₄). and evaporated in vacuo to a brown solid (650 mg). A stirred solution of the solid in ethanol (10 ml) and 2M NaOH (16 ml) was heated at reflux under argon for 18 h. The mixture was concentrated in vacuo, partitioned between ethyl acetate and water and the aqueous further extracted with ethyl acetate (3×). The combined organics were dried (Na₂SO₄) and evaporated in vacuo to the title compound as a pale brown solid (403 mg, 35%).

¹H NMR (250 MHz, d⁶DMSO) δ(ppm): 7.01 (d, 1H), 6.57 (d, 1H), 6.42 (dd, 1H), 5.19 (s, 2H), 2.92 (m, 2H), 2.73 (m, 1H), 2.21 (s, 3H), 1.97 (m, 2H), 1.64 (m, 4H).

DESCRIPTION 8
5-(Pyridin-4-yl)-1-naphthoic Acid

The title compound was prepared from 4-pyridylboronic acid and 5-bromo-1- naphthoic acid (J. Chem. Soc., 1950, 991) using a similar procedure to Example 4, obtained as a white solid (55%).

¹H NMR (250 MHz, d⁶DMSO) δ(ppm:) 8.97 (d, 1H), 8.73 (d, 2H), 8.16 (d, 1H), 7.95 (d, 1H), 7.42 (t, 1H), 7.57 (m, 4H). Acid proton was not observed.

DESCRIPTION 9
1-Acetyl-2,3-dihydro-6-nitro-1H-indole

A stirred solution of 2,3-dihydro-6-nitro-1H-indole (100 g, 0.61 mole) in dichloromethane (1000 ml) at room temperature was treated dropwise over 20 minutes with acetic anhydride (62 ml, 0.66 mole). The reaction mixture was stirred for a further 2 h, then washed with 10% Na₂CO₃ solution (300 ml) dried (Na₂SO₄) and concentrated in vacuo to afford the title compound as a yellow solid (125 g, 100%).

DESCRIPTION 10
1-Acetyl-2,3-dihydro-6-amino-1H-indole

A stirred suspension of 1-acetyl-2,3-dihydro-6-nitro-1H-indole (D9, 125 g, 0.61 mole) in THF (5500 ml) was hydrogenated over 10% Pd-C (20 g) at 50 psi for 20 h. The catalyst was removed by filtration through a plug of kieselguhr and the filtrate concentrated in vacuo to afford the title compound as a beige solid (102 g, 95%).

¹H NMR (250 MHz, CDCl₃) δ(ppm): 7.64 (d, 1H), 6.92 (d, 1H), 6.34 (dd, 1H), 4.01 (t, 2H), 3.82 (br s, 2H), 3.06 (t, 2H), 2.19 (s, 3H).

DESCRIPTION 11
1-Acetyl-2,3-dihydro-6-(4-methylpiperazin-1-yl)-1H-indole

A stirred mixture of 1-acetyl-6-amino-2,3-dihydro-1H-indole (D10, 37.8 g, 0.22 mole), mechlorethamine hydrochloride (46 g, 0.24 mole) and anhydrous potassium carbonate (80 g, 0.58 mole) in 1-butanol (1800 ml) was heated at reflux for 8 h, then additional mechlorethamine hydrochloride (25 g, 0.13 mole) and potassium carbonate (41 g, 0.30 mole) were added and reflux continued for 3 h. The reaction mixture was allowed to cool and then washed with water (1000 ml). The aqueous wash was extracted with ethyl acetate, and the extract combined with the 1-butanol solution and concentrated in vacuo. The brown oily residue (60 g) was chromatographed on silica gel eluting with 0–8% MeOH/DCM to give an orange oil, which was trituated with ether to afford the title compound as a beige solid (12.2 g, 22%).

¹H NMR (250 MHz, CDCl₃) δ(ppm): 7.98 (d, 1H), 7.04 (d, 1H), 6.59 (dd, 1H), 4.04 (t, 2H), 3.23–3.18 (m, 4H), 3.10 (t, 2H), 2.60–2.53 (m, 4H), 2.34 (s, 3H), 2.21 (s, 3H).

DESCRIPTION 12
1-Acetyl-5-bromo-2,3-dihydro-6-(4-methylpiperazin-1-yl)-1H-indole A stirred mixture of 1-acetyl-2,3-dihydro-6-(4-methylpiperazin-1-yl)-1H-indole (D11, 2.0 g, 0.0077 mole) and anhydrous potassium carbonate (2.12 g, 0.015 mole) in a mixture of dichloromethane (100 ml) and methanol (50 ml) at −5° C. under argon was treated portionwise over 20 minutes with benzyltrimethylammonium tribromide (3.14 g, 0.0081 mole). The mixture was allowed to warm to room temperature over 1 h, then concentrated in vacuo and the residue dissolved in dichloromethane (150 ml), washed with water (2×100 ml), dried ($Na_2SO_4$) and concentrated in vacuo to afford the title compound as a beige solid (2.52 g, 97%).

$^1$HNMR (250 MHz, $CDCl_3$) δ(ppm): 8.06 (s, 1H), 7.34 (s, 1H), 4.06 (t, 2H), 3.13 (t, 2H), 3.07 (br s, 4H), 2.06 (br s, 4H), 2.35 (s, 3H), 2.21 (s, 3H).

DESCRIPTION 13
5-Bromo-2,3-dihydro-6-(4-methylpiperazin-1-yl)-1H-indole

A solution of 1-acetyl-5-bromo-6-(4-methylpiperazin-1-yl)-1H-indole (D12, 0.60 g, 1.8 mmole) in 2M hydrobromic acid (50 ml) was stirred at room temperature for 5 days, then basified by addition of solid $K_2CO_3$ and extracted with DCM. The extract was dried ($Na_2SO_4$) and concentrated in vacuo to afford the title compound as a brown solid (0.31 g, 58%).

$^1$H NMR (250 MHz, $CDCl_3$) δ(ppm): 7.24 (s, 1H), 6.42 (s, 1H), 3.80 (br s, 1H), 3.56 (t, 2H), 3.01–2.92 (m, 6H), 2.59 (br s, 4H), 2.35 (s, 3H).

EXAMPLE 1
4-Bromo-N-[4-methoxy-3-(4-methylpiperazin-1-yl)phenyl]naphth-1-yl Carboxamide A mixture of 4-bromo-1-naphthoic acid (400 mg, 1.6 mmole) in thionyl chloride (10 ml) was heated under reflux for 2 h, then concentrated in vacuo to afford the acid chloride. This was dissolved in dichloromethane (15 ml) and treated with 4-methoxy-3-(4-methylpiperazin-1-yl)aniline (350 mg, 1.6 mmol, EP 0533268A1) and triethylamine (0.22 ml, 1.6 mmole). The reaction mixture was stirred at room temperature for 20 hours, then concentrated in vacuo and the residue partitioned between water and chloroform. The organic layer was separated, dried ($Na_2SO_4$) and concentrated. The residue was purified by flash chromatography on silica gel eluting with 1% methanol/chloroform. Trituration of the product with 60–80 petrol ether afforded the title compound as a yellow solid (130 mg, 18%).

$^1$H NMR (250 MHz, $CDCl_3$) δ(ppm): 8.43–8.27 (m, 2H), 7.79 (d, 1H), 7.75–7.50 (m, 4H), 7.35 (dd, 1H), 7.22 (d, 1H), 6.86 (d, 1H), 3.90 (s, 3H), 3.10 (br s, 4H), 2.60 (br s, 4H), 2.38 (s, 3H).

EXAMPLE 2
5-Bromo-N-[4-methoxy-3-(4-methylpiperazin-1-yl)phenyl]naphth-1-yl Carboxamide The title compound was prepared from 5-bromo-1-naphthoic acid (J. Chem. Soc., 1950, 991) and 4-methoxy-3-(4-methylpiperazin-1-yl)aniline (EP0533268A1) using a similar procedure to Example 1.

$^1$H NMR (HCl salt) (250 MHz, $d^6$DMSO) δ(ppm): 11.00 (br s, 1H), 10.51 (s, 1H), 8.30 (d, 1H), 8.21 (d, 1H), 7.98 (d, 1H), 7.88–7.73 (m, 2H), 7.58–7.43 (m, 3H), 6.99 (d, 1H), 3.80 (s, 3H), 3.57–3.42 (m, 3H), 3.30–2.96 (m, 4H), 2.80 (d, 3H).

EXAMPLE 3
N-[4-Methoxy-3-(4-methylpiperazin-1-yl)phenyl]quinolin-4-yl Carboxamide The title compound was prepared from quinoline-4-carboxylic acid and 4-methoxy-3-(4-methylpiperazin-1-yl)aniline (EP0533268A1) using a similar procedure to Example 1.

$^1$H NMR (250 MHz, $CDCl_3$) δ(ppm):8.84 (s, 1H), 8.61 (d, 1H), 8.11 (d, 1H), 7.93 (t, 1H), 7.38 (m, 2H), 7.35 (d, 1H), 6.88 (d, 1H), 6.76 (d, 1H), 3.80 (s, 3H), 3.02 (br s, 4H), 2.54 (br s, 4H), 2.26 (s, 3H).

EXAMPLE 4
N-[4-Methoxy-3-(4-methylpiperazin-1-yl)phenyl]-5-(pyridin-4-yl)naphth-1-yl Carboxamide A stirred suspension of 5-bromo-N-[4-methoxy-3-(4-methylpiperazin-1-yl)phenyl]naphth-1-yl carboxamide hydrochloride salt (E2, 0.35 g, 0.71 mmole) and 4-pyridylboronic acid (85 mg, 0.71 mmole) in 1,2-dimethoxyethane (30 ml) and water (30 ml) containing sodium carbonate (0.38 g, 3.5 mmole) was de-gassed by bubbling argon through for 15 minutes. Tetrakis (triphenylphosphine)palladium (0) (80 mg) was added and the mixture heated at reflux for 30 h. The mixture was concentrated in vacuo to approx. 30 ml volume, then diluted with water (50 ml) and extracted with dichloromethane. The organic extract was dried ($Na_2SO_4$) and concentrated in vacuo to a dark solid. Purification by column chromatography on silica gel eluting with 0–20% methanol/dichloromethane afforded the title compound as a pale yellow oil (55 mg, 17%). This was converted to its hydrochloride salt and solidified from acetone.

$^1$H NMR (free base) (250 MHz, $CDCl_3$) δ(ppm): 8.74 (d, 2H), 8.45 (d, 1H), 7.94 (d, 1H), 7.80–7.70 (m, 2H), 6.67–7.58 (m, 1H), 7.55–7.33 (m, 6H), 6.89 (d, 1H), 3.90 (s,3H), 3.15 (br s, 4H), 2.63 (br s, 4H), 2.37 (s, 3H).

EXAMPLE 5
N-[4-Methoxy-3-(4-methylpiperazin-1-yl)phenyl]-4-(pyridin-4-yl)naphth-1-ylcarboxamide The title compound was prepared from 4-bromo-N-[4-methoxy-3-(4-methylpiperazin-1-yl)phenyl]naphth-1-ylcarboxamide (E1) and 4-pyridylboronic acid following a similar procedure to Example 4.

$^1$H NMR (250 MHz, $CDCl_3$) δ(ppm): 8.74 (d, 2H), 8.46 (d, 1H), 7.90–7.75 (m, 3H), 7.68–735 (m, 6H), 6.88 (d, 1H), 3.89 (s, 3H), 3.15 (br s, 4H), 2.67 (br s, 4H), 2.38 (s, 3H). 1H not discernible from spectrum.

EXAMPLE 6
N-[(4-Methoxy-3-(4-methylpiperazin-1-yl)phenyl]-N'-[naphth-1-yl]urea A solution of naphth-1-yl isocyanate (76 mg, 0.45 mmole) in dichloromethane (2 ml) was added to a solution of 4-methoxy-3-(4-methylpiperazin-1-yl)aniline (100 mg, 0.45 mmole, EP0533268A1) in dichloromethane (2 ml) and the reaction mixture was agitated at room temperature for 18 h. The dichloromethane was then allowed to evaporate off over 24 h. Trituration of the residue with ethyl acetate and filtration afforded the title compound as a white crystalline solid (85 mg, 48%).

$^1$H NMR (250 MHz, $d^6$DMSO) δ(ppm): 8.88 (s,1H), 8.65 (s, 1H), 8.12 (d, 1H), 8.02 (d, 1H), 7.92 (d, 1H), 7.52 (m, 4H), 7.05 (m, 2H), 6.87 (d, 1H), 3.75 (s, 3H), 2.97 (m, 4H), 2.46 (m, 4H), 2.22 (s, 3H).

EXAMPLE 7
N-[4-Bromonaphth-1-yl]-N'-[(4-methoxy-3-(4-methylpiperazin-1-yl)phenyl]urea A stirred solution of 4-methoxy-3-(4-methylpiperazin-1-yl)aniline (1.0 g, 4.5 mmole, EP0533268A1 ) in dichloromethane (20 ml) was treated with 1,1'-carbonyldiimidazole (0.80 g, 4.9 mmole) and the mixture stirred at room temperature under argon for 0.5 h., then concentrated in vacuo. The residue was dissolved in dimethylformamide (20 ml) and 4-bromonaphth-1-ylamine (1 g, 4.5 mmole) was added and the mixture stirred at room temperature under argon for 18 h. The mixture was diluted with water (50 ml) and extracted with dichloromethane (2×50 ml). The extract was dried (Na2SO$_4$) and concentrated in vacuo to leave a brown solid, which was triturated with ethyl acetate. The solid was filtered off to afford the title compound as a white solid (0.76 g, 36%).

MS: m/z=469/471 (MH$^+$)

EXAMPLE 8
N-[4-Methoxy-3-(4-methylpiperazin-1-yl)phenyl]-N'-[4-(pyridin-4-yl)naphth-1-yl]urea The title compound was prepared from N-[4-bromonaphth-1-yl]-N'-[(4-methoxy-3-(4-methylpiperazin-1-yl)phenyl]urea (E7) using a similar procedure to Example 4.

$^1$H NMR (250 MHz, CDCl$_3$) δ(ppm): 8.61 (d, 2H), 7.86 (m, 1H), 7.77 (d, 1H), 770 (m, 1H), 7.62 (s, 1H), 7.49 (s, 1H), 7.25 (m, 5H), 6.91 (m, 2H), 6.63 (m, 1H), 3.72 ( s, 3H), 2.96 (m, 4H), 2.50 (m, 4H), 2.25 (s, 3H).

EXAMPLE 9
4-Bromo-N-[4-methoxy-3-(4-methylpiperizin-1-yl)phenyl] naphth-1-yl Acetamide The title compound was prepared from 4-bromonaphth-1-ylacetic acid (J. Org. Chem., 1951, 16, 1588) and 4-methoxy-3-(4-methylpiperazin-1-yl)aniline (EP0533268A1) following a similar procedure to Example 1.

$^1$H NMR (250 MHz, CDCl$_3$) δ(ppm): 8.19 (d, 1H), 7.79 (d, 1H), 7.65 (d, 2H), 7.55–7.35 (m, 2H), 7.15 (d, 1H), 6.87 (d, 2H), 6.55 (d, 1H), 3.89 (s,2H), 3.68 (s, 3H), 3.10–2.81 (s, 4H), 2.60–2.35 (s, 4H), 2.23 (s, 3H)

EXAMPLE 10
N-[4-Methoxy-3-(4-methylpiperazin-1-yl)phenyl]-4-(pyridin-4-yl)naphth-1-ylacetamide The title compound was prepared from 4-(pyridin-4-yl) naphth-1-ylacetic acid (D2) and 4-methoxy-3-(4-methylpiperazin-1-yl)aniline (EP0533268A1) following a similar procedure to Example 1.

$^1$H NMR (250 MHz, CDCl$_3$) δ(ppm): 8.75 (dd, 2H), 8.15 (d, 1H), 7.9 (d, 1H), 7.65–7.4 (m, 6H), 7.2 (s, 1H), 7.03–6.9 (m, 2H), 6.7 (d, 1H), 4.2 (s, 2H), 3.8 (s, 3H), 3.05 (br s, 4H), 2.6 (br s, 4H), 2.35 (s, 3H).

EXAMPLE 11
N-[4-Chloro-3-(4-methylpiperazin-1-yl)phenyl]-N'-[4-(pyridin-4-yl)naphth-1-yl]urea To a stirred solution of triphosgene (39 mg, 0.13 mmole) in dichloromethane (10 ml) was added a solution of 4-(pyridin-4-yl)naphth-1-ylamine (D1, 82 mg, 0.37 mmole) and triethylamine (0.05 ml, 0.37 mmole) dropwise over 30 minutes. When the addition was complete the mixture was stirred at room temperature for 15 minutes, then a solution of 4-chloro-3-(4-methylpiperazin-1-yl)aniline (100 mg, 0.44 mmole, EP0533268A1) in dichloromethane (10 ml) was added over 5 minutes. After 18 h, the mixture was washed with 10% aqueous sodium carbonate solution and water, dried (Na$_2$SO$_4$) and evaporated to dryness. The residue was purified by column chromatography on silica gel eluting with 10% methanol/dichloromethane and the title compound was obtained as a white solid on trituration with ether (47 mg, 27%).

$^1$H NMR (250 MHz, CDCl$_3$) δ(ppm): 8.71 (d, 2H), 8.05–7.96 (m, 1H), 7.86–7.71 (m, 2H), 7.55–7.39 (m, 4H), 7.36–7.28 (m, 3H), 7.20–7.13 (m, 2H), 6.87 (dd, 1H), 3.00 (br s, 4H), 2.55 (br s, 4H), 2.33 (s, 3H).

EXAMPLE 12
N-[4-Methoxy-3-(4-methylpiperazin-1-yl)phenyl]-N'-[naphth-1-yl]thiourea The title compound was prepared from 1-naphthyl isothiocyanate and 4-methoxy-3-(4-methylpiperazin-1-yl) aniline (EP0533268A1) using a similar procedure to Example 6.

MS: m/z=407 (MH$^+$)

EXAMPLE 13
N-[4-Methoxy-3-(1-methylpiperidin-4-yl)phenyl]-N'-[4-(pyridin-4-yl)naphth-1-yl]urea The title compound was prepared from 4-(pyridin-4-yl) naphth-1-ylamine (D1) and 4-methoxy-3-(1-methylpiperidin-4-yl)aniline (Description 3 in WO 96/31508) using a similar procedure to Example 11.

$^1$H NMR (250 MHz, CDCl $_3$) δ(ppm): 8.68 (d, 2H), 8.22 (br s, 1H), 8.18–8.10 (m, 1H), 8.07 (br s, 1H), 7.97 (d, 1H), 7.85–7.76 (m, 1H), 7.56 (dd, 1H), 7.45–7.37 (m, 2H), 7.35–7.28 (m, 3H), 7.07 (d, 1H), 6.75 (d, 1H), 3.75 (s, 3H), 3.07–2.85 (m, 3H), 2.40 (s, 3H), 2.30–2.17 (m, 2H), 1.90–1.67 (m, 4H).

EXAMPLE 14
N-[4-Methoxy-3-(4-methylpiperazin-1-yl)phenyl]-N'-[5,6,7,8-tetrahydronaphth-1-yl]urea The title compound was prepared from 5,6,7,8-tetrahydronaphth-1-ylamine and 4-methoxy-3-(4-methylpiperazin-1-yl)aniline (EP0533268A1) using a similar procedure to Example 11.

$^1$H NMR (HCl salt) (250 MHz, d$^6$DMSO) δ(ppm): 10.57 (br s, 1H), 9.32 (s, 1H), 7.97 (s, 1H), 7.63 (d, 1H), 7.21 (d, 1H), 7.03–6.97 (m, 2H), 6.88 (d, 1H), 6.73 (d, 1H), 3.76 (s, 3H), 3.49 (d, 4H), 3.25–3.15 (m, 2H), 3.02–2.93 (m, 2H), 2.82 (d, 3H), 2.71 (t, 2H), 2.59 (t, 2H), 1.85–1.65 (m, 4H).

EXAMPLE 15
N-[Indian-5-yl]-N'-[4-methoxy-3-(4-methylpiperazin-1-yl) phenyl]urea The title compound was prepared from 5-aminoindan and 4-methoxy-3-(4-methylpiperazin-1-yl)aniline (EP0533268A1) using a similar procedure to Example 11.

$^1$H NMR (HCl salt) (250 MHz, d$^6$DMSO) δ(ppm): 10.86 (br s, 1H), 9.17 (s, 1H), 9.16 (s, 1H), 7.51 (s, 1H), 7.34 (d, 1H), 7.26 (dd, 1H), 7.20 (d, 1H), 7.11 (dd, 1H), 7.01 (d, 1H), 3.88 (s, 3H), 3.60 (d, 4H), 3.38–3.26 (m, 2H), 3.18–3.06 (m, 2H), 2.98–2.88 (m, 7H), 2.18–2.06 (m, 2H).

EXAMPLE 16
N-[Benzo-2,1,3-thiadiazol-4-yl]-N'-[4-methoxy-3-(4-methylpiperazin-1-yl)phenyl]urea The title compound was prepared from 4-aminobenzo-2, 1,3-thiadiazole and 4-methoxy-3-(4-methylpiperazin-1-yl) aniline (EP0533268A1) using a similar procedure to Example 11.

$^1$H NMR (250 MHz, CDCl$_3$) δ(ppm): 8.45 (s, 1H), 8.34–8.32 (m, 1H), 7.81 (s, 1H), 7.57–7.55 (m, 2H), 7.17

(dd, 1H), 6.91 (d, 1H), 6.85 (d. 1H), 3.87 (s, 3H), 3.13 (br s, 4H), 2.67 (br s, 4H), 2.39 (s, 3H).

EXAMPLE 17
N-[Indol-4-yl]-N'-[4-methoxy-3-(4-methylpiperazin-1-yl) phenyl]urea The title compound was prepared from 4-aminoindole and 4-methoxy-3-(4-methylpiperazin-1-yl)aniline (EP0533268A1) using a similar procedure to Example 11.

$^1$H NMR (250MHz, CDCl$_3$) δ(ppm): 9.08 (s, 1H), 7.79 (s, 1H), 7.68 (s, 1H), 7.64 (t, 1H), 7.15–7.13 (m, 3H), 7.08 (dd, 1H), 7.04 (d, 1H), 6.78 (d, 1H), 6.58 (m, 1H), 3.83 (s, 3H), 3.10 (br s, 4H), 2.63 (br s, 4H), 2.36 (s, 3H).

EXAMPLE 18
N-[4-Methoxy-3-(4-methylpiperazin-1-yl)phenyl]-N'-[3,4-methylenedioxyphenyl]urea The title compound was prepared from 3,4-methylenedioxyphenyl isocyanate and 4-methoxy-3-(4-methylpiperazin-1-yl)aniline (EP0533268A1) using a similar procedure to Example 11.

$^1$H NMR (250MHz, CDCl$_3$) δ(ppm): 6.98 (d, 1H), 6.94 (dd, 1H), 6.86 (d, 1H), 6.78 (d, 1H), 6.75–6.66 (m, 3H), 6.62 (dd, 1H), 5.92 (s, 2H), 3.84 (s, 3H), 3.07 (br s, 4H), 2.61 (br s, 4H), 2.34 (s, 3H).

EXAMPLE 19
N-[-Bromonaphth-1-yl]-N'-[4-methoxy-3-(4-methylpiperazin-1-yl)phenyl]urea To a stirred solution of 5-bromonaphth-1-yl isocyanate (D4, 3.2 g, 0.013 mol) in dichloromethane (150 ml) was added 4-methoxy-3-(4-methylpiperazin-1-yl)aniline (EP 0533268 A1) in dichloromethane. After 2 hours the reaction was concentrated in vacuo and the residue saturated with ether to give the title compound (82%).

$^1$H NMR (250 MHz, d$^6$DMSO) δ(ppm): 8.7 (s, 1H), 8.6 (s, 1H), 8.05–7.90 (m, 2H), 7.8–7.65 (m, 2H), 7.5 (t, 1H), 7.3 (t, 1H), 6.9 (m, 2H), 6.7 (d, 1H), 3.6 (s, 3H), 2.8 (br s, 4H), 2.25 (br s, 4H), 2.05 (s, 3H).

EXAMPLE 20
5-Bromo-N-[4-methoxy-3-(4-methylpiperazin-1-yl)phenyl] naphth-1-ylacetamide 5-Bromo-1-naphthylacetic acid (Bull. Soc. Chim. Fr 1968, 71, 2957, 4.7 g, 17.8 mmol) in dichloromethane (150 ml) was treated with oxalyl chloride (4.7 ml, 53.4 mmol) and a drop of dimethylformamide under an atmosphere of argon with stirring for 1.5 hours. The reation was then concentrated in vacuo to a gum which was azeotroped with toluene to remove excess oxalyl chloride. The acid chloride was dissolved in dichloromethane (100 ml) and treated with 4-methoxy-3-(4-methylpiperazin-1-yl)aniline (EP 0533268A 1, 3.9 g, 17.8 mmol,) and triethylamine (2 ml) and the reaction stirred at room temp. overnight. The reaction was washed with saturated aqueous potassium carbonate solution, dried (Na$_2$SO$_4$) and concentrated in vacuo to give the title compound as needles from ethanol (3.7 g, 50%).

$^1$H NMR (250 MHz, d$^6$DMSO) δ(ppm): 8.2 (d, 1H), 8.1 (d, 1H), 7.9 (d, 1H), 7.7–7.4 (m, 4H), 7.2 (m, 2H), 6.8 (d, 1H), 4.15 (s, 2H), 3.75 (s, 3H), 2.9 (br s, 4H), 2.4 (br s, 4H), 2.2 (s, 3H).

EXAMPLE 21
N-[4-Methoxy-3-(4-methylpiperazin-1-yl)phenyl]-N'-[2-methylquinolin-6-yl]urea The title compound was prepared from 6-amino-2-methylquinoline and 4-methoxy-3-(4-methylpiperazin-1-yl) aniline (EP 0533268A1) using a similar procedure to Example 11.

$^1$H NMR (250 MHz, CDCl$_3$) δ(ppm): 8.08 (d, 1H), 7.95 (d, 1H), 7.89 (d, 1H), 7.37 (dd,1H), 7.22 (d, 1H), 7.21 (s, 1H), 6.99 (dd, 1H), 6.89 (d, 1H), 6.81 (d, 1H), 3.86 (s, 3H), 3.08 (br s, 4H), 2.71 (s, 3H), 2.60 (br s, 4H), 2.34 (s,3H).

EXAMPLE 22
N-[Isoquinolin-5-yl]-N'-[4-methoxy-3-(4-methylpiperazin-1-yl)phenyl]urea The title compound was prepared from 5-aminoisoquinoline and 4-methoxy-3-(4-methylpiperazin-1-yl)aniline (EP 0533268A1) using a similar procedure to Example 11.

$^1$H NMR (250 MHz, CDCl$_3$) δ(ppm): 9.14 (s, 1H), 8.34 (d, 1H), 8.06 (d, 1H), 7.73 (s, 1H), 7.64 (d, 1H), 7.54 (d, 1H), 7.54 (s, 1H), 7.48 (t, 1H), 6.97 (dd, 1H), 6.92 (d, 1H), 6.73 (d, 1H), 3.81 (s, 3H), 3.03 (br s, 4H), 2.56 (br s, 4H), 2.56 (br s, 4H), 2.31 (s, 3H).

EXAMPLE 23
N-[Benzothiazol-6-yl]-N'-[4-methoxy-3-(4-methylpiperazin-1-yl)phenyl]urea The title compound was prepared from 6-aminobenzothiazole and 4-methoxy-3-(4-methylpiperazin-l-yl)aniline (EP 0533268A1) using a similar procedure to Example 11.

$^1$H NMR (250 MHz, CDCl$_3$) δ(ppm): 8.86 (s, 1H), 8.32 (d, 1H), 7.96 (d, 1H), 7.45 (s, 1H), 7.19 (dd, 1H), 7.07 (s, 1H), 7.00 (dd, 1H), 6.85 (d, 1H), 6.78 (d, 1H), 3.83 (s, 3H), 3.07 (brs, 4 H), 2.62 (brs, 4H), 2.35 (s, 3H).

EXAMPLE 24
N-[4-Methoxy-3-(4-methylpiperazin-1-yl)phenyl]-N-[quinolin-3-yl]urea The title compound was prepared from 3-aminoquinoline and 4-methoxy-3-(4-methylpiperazin-1-yl)aniline (EP 0533268A1) using a similar procedure to Example 11.

$^1$H NMR (250 MHz, CDCl$_3$) δ(ppm): 8.58 (d, 1H), 8.55 (d, 1H), 7.99 (d, 1H), 7.74 (d, 1H), 7.57 (dt, 1H), 7.48 (dt, 1H), 7.43 (s, 1H), 7.03 (s, 1H), 7.01 (dd, 1H), 6.90 (d, 1H), 6.82 (d, 1H), 3.85 (s, 3H), 3.08 (brs, 4H), 2.59 (brs, 4H), 2.34 (s, 3H).

EXAMPLE 25
N-[4-Methoxy-3-(4-methylpiperazin-1-yl]phenyl-N'-[quinolin-6-yl]urea The title compound was prepared from 6-aminoquinoline and 4-methoxy-3-(4-methylpiperazin-1-yl)aniline (EP 0533268A1) using a similar procedure to Example 11.

$^1$H NMR (250 MHz, CDCl$_3$) δ(ppm): 8.79 (dd, 1H), 8.14 (d, 1H), 8.05 (dd, 1H), 7.97 (d, 1H), 7.43–7.32 (m, 3H), 6.99 (dd, 1H), 6.93 (s, 1H), 6.89 (d, 1H), 6.81 (d, 1H), 3.85 (s, 3H), 3.08 (br s, 4H), 2.60 (br s, 4H), 2.34 (s, 3H).

EXAMPLE 26
N-[4-Methoxy-3-(4-methylpiperazin-1-yl)phenyl]-N'[-quinolin-5-yl]urea The title compound was prepared from 5-aminoquinoline and 4-methoxy-3-(4-methylpiperazin-1-yl)aniline (EP 0533268A1) using a similar procedure to Example 11.

$^1$H NMR (250 MHz, CDCl$_3$) δ(ppm): 8.83 (dd, 1H), 8.12 (dd, 1H), 7.87 (d, 1H), 7.69 (d, 1H), 7.57 (t, 1H), 7.42 (s, 1H), 7.22 (dd, 1H), 7.17 (s, 1H), 6.90 (s, 1H), 6.88 (dd, 1H), 6.69 (d, 1H), 3.80 (s, 3H), 3.02 (brs, 4H), 2.56 (brs, 4H), 2.31 (s, 3H).

EXAMPLE 27

N-[2,3-Dihydrobenzofuran-5-yl]-N'-[4-methoxy-3-(4-methylpiperazin-1-yl)phenyl]urea To a stirred solution of 2,3-dihydrobenzofuran-5-yl isocyanate (D3, 0.248 g, 1.5 mmol) in $CH_2Cl_2$ (20 ml) was added to a solution of 4-methoxy-3-(4-methylpiperazin-1-yl)aniline (EP 0533268A1, 0.309 g, 1.4 mmol) in $CH_2Cl_2$ (10 ml). After 18 hours a precipitate had formed which was filtered off, washed with $CH_2Cl_2$ and dried under vacuum to afford the title compound as a cream coloured solid (0.253 g, 47%).

$^1$H NMR (250 MHz, $CDCl_3$) δ(ppm):. 7.61 (s, 1H), 7.55 (s, 1H), 7.43 (d, 1H), 7.07 (d, 1H), 6.98 (dd, 1H), 6.94 (dd, 1H), 6.76 (d, 1H), 6.68 (d, 1H), 4.54 (t, 2H), 3.83 (s, 3H), 3.18 (t, 2H), 3.10 (br s, 4H), 2.59 (br s, 4H), 2.35 (s, 3H).

EXAMPLE 28

N-[4-Methoxy-3-(4-methylpiperazin-1-yl)phenyl]-4-(pyridin-3-yl)naphth-1-ylacetamide The title compound was prepared from 4-bromo-N-[4-methoxy-3-(4-methyipiperazin-1-yl)phenyl]-1-naphthylacetamide (E9) and 3-pyridylboronic acid using a similar procedure to Example 4 as a white solid (32%).

$^1$H NMR (250 MHz, $CDCl_3$) δ(ppm): 8.7 (m, 2H), 8.15 (d, 1H), 7.85 (m, 2H), 7.47–738 (m, 6H), 7.02–6.95 (m, 2H), 6.71 (d, 1H), 4.19 (s, 2H), 3.79 (s, 3H), 3.03 (s, 4H), 2.57 (s, 4H), 2.32 (s, 3H).

EXAMPLE 29

N-[4-Methoxy-3-(4-methylpiperazin-1-yl)phenyl]-N'-[5-(pyridin-3-yl)naphth-1-yl]urea The title compound was prepared from N-[5-bromo-1-naphthyl]-N'-[4-methoxy-3-(4-methylpiperazin-1-yl)phenyl]urea (E19) and 3-pyridylboronic acid using a similar procedure to Example 4 as a white solid (28%).

$^1$H NMR (250 MHz, $CDCl_3$) δ(ppm): 8.70 (m,2H), 7.85 (d, 1H), 7.75 (d, 2H), 7.60 (d, 1H) 7.42–7.40 (m, 4H), 7.18 (s, 1H), 6.95 (m, 3H), 6.78 (d, 1H), 3.83 (s, 3H) 3.06 (s, 4H), 2.58 (s, 4H), 2.33 (s, 3H).

EXAMPLE 30

4-(4-Acetylphenyl)-N-4-methoxy-3-(4-methylpiperazin-1-yl)phenyl]naphth-1-ylacetamide The title compound was prepared from 4-bromo-N-[4-methoxy-3-(4-methylpiperazin-1-yl)phenyl]naphth-1-ylacetamide (E9) and 4-acetylphenylboronic acid using a similar procedure to Example 4 as a pale yellow powder (73%).

$^1$H NMR (250 MHz, $CDCl_3$) δ(ppm): 8.12 (m, 3H), 7.90 (d, 1H), 7.63–7.42 (m, 6H), 7.00–6.90 (m, 3H), 6.73 (d, 1H), 4.21 (s, 2H), 3.80 (s, 3H), 3.04 (brs, 4H), 2.70 (s, 3H), 2.58 (brs, 4H), 2.33 (s, 3H).

EXAMPLE 31

4-(3-Acetylphenyl)-N-[4-methoxy-3-(4-methylpiperazin-1-yl phenyl]naphth-1-ylacetamide The title compound was prepared from 4-bromo-N-[4-methoxy-3-(4-methylpiperazin-1-yl)phenyl]naphth-1-ylacetarnide (E9) and 3-acetylphenylboronic acid using a similar procedure to Example 4 as a yellow powder (84%).

$^1$H NMR (HCl salt) (250 MHz, $d^6$DMSO)δppm: 10.67 (bs, 1H), 10.26 (s, 1H), 8.13 (d, 1H), 7.92 (d, 1H), 7.85 (2, 1H), 7.64–7.28 (m, 7H), 7.21 (d, 1H), 7.12 (dd, 1H), 4.64 (s, 2H), 3.60 (s, 3H), 3.32 (d, 4H), 3.04 (m, 2H), 2.81 (m, 2H), 2.65 (d, 3H), 2.49 (s, 3H).

EXAMPLE 32

5-(3-Acetylphenyl)-N-[4-methoxy-3-(4-methylpiperazin-1-yl)phenyl]naphth-1-ylacetamide The title compound was prepared from 5-bromo-N-[4-methoxy-3-(4-methylpiperazin-1-yl)phenyl]naphth-1-ylacetarnide (E20) and 3-acetylboronic acid using a similar procedure to Example 4 as a pale buff powder (74%).

$^1$H NMR (HCl salt) (250 MHz, $d^6$DMSO) δ(ppm): 11.04 (bs, 1H), 10.56 (s, 1H), 8.40 (d, 1H), 8.22 (d, 1H), 8.15 (s, 1H), 7.90–7.61 (m, 8H), 7.52 (d, 1H), 7.43 (dd, 1H), 4.35 (s, 2H), 3.91 (s, 3H), 3.60 (bd, 4H), 3.30 (m, 2H), 3.12 (m, 2H), 2.93 (d, 3H), 2.79 (s, 3H).

EXAMPLE 33

N-[4-Methoxy-3-(4-methylpiperazin-1-yl)phenyl]-N'-[5-phenylnaphth-1-yl]urea

The title compound was prepared from N-[5-bromonaphth-1-yl]-N'-[4-methoxy-3-(4-methylpiperazin-1-yl)phenyl]urea (E19) and phenylboronic acid using a similar procedure to Example 4 (47%).

$^1$H NMR (250 MHz, $d^6$DMSO) δ(ppm): 9.1 (s, 1H), 8.9 (s, 1H), 8.3 (d. 1H), 8.15 (d, 1H), 7.8–7.5 (m, 9H), 7.25–7.15 (m, 2H), 7.0 (d, 1H), 3.9 (s, 3H), 3.1 (br s, 4H), 2.6 (brs s, 4H), 2.4 (s, 3H).

EXAMPLE 34

N-[4-Methoxy-3-(4-methylpiperazin-1-yl)phenyl]-5-(pyridin-3-yl)naphth-1-ylacetamide The title compound was prepared from 5-bromo-N-[4-methoxy-3-(4-methylpiperazin-1-yl)phenyl]naphth-1-ylacetamide (E20) and 3-pyridylboronic acid using a similar procedure to Example 4 (13%).

$^1$H NMR (250 MHz, $CDCl_3$) δ(ppm): 8.7 (m, 2H), 8.1 (d, 1H), 7.75 (m, 2H), 7.6–7.35 (m, 6H), 7.05–6.9 (m, 2H), 6.7 (d, 1H), 4.15 (s, 2H), 3.8 (s, 3H), 3.0 (br s, 4H), 2.55 (br s, 4H), 2.3 (s, 3H).

EXAMPLE 35

N-[4-Methoxy-3-(4-methylpiperazin-1-yl)phenyl]-5-phenylnaphth-1-ylacetamide

The title compound was prepared from 5-bromo-N-[4-methoxy-3-(4-methylpiperazin-1-yl)phenyl]naphth-1-ylacetamide (E20) and phenylboronic acid using a similar procedure to Example 4 (39%).

$^1$H NMR (250 MHz, $CDCl_3$) δ(ppm): 8.1 (d, 1H), 7.9 (d, 1H), 7.6–7.4 (m, 10H), 6.9 (m, 2H), 6.7 (d, 1H), 4.2 (s, 2H), 3.7 (s, 3H), 3.05 (br s, 4H), 2.6 (br s, 4H), 2.6 (br s, 4H), 2.35 (s, 3H).

EXAMPLE 36

5-(4-Acetylphenyl)-N-[4-methoxy-3-(4-methylpiperazin-1-yl)phenyl]naphth-1-ylacetamide The title compound was prepared from 5-bromo-N-[4-methoxy-3-(4-methylpiperazin-1-yl)phenyl]naphth-1-ylacetamide (E20) and 4-acetylphenylboronic acid using a similar procedure to Example 4 (20%).

$^1$H NMR (250 MHz, $CDCl_3$) δ(ppm): 8.1 (d, 2H), 7.85 (d, 1H), 7.7–7.4 (m, 7H), 6.95 (m, 3H), 6.7 (d, 1H), 4.2 (s, 2H), 3.8 (s, 3H), 3.05 (br s, 4H), 2.7 (s, 3H) 2.6 (br s, 4H), 2.2 (s, 3H).

EXAMPLE 37

N-[4-Methoxy-3-(4-methylpiperazin-1-yl)phenyl]-5-(2-methylphenyl)naphth-1-ylacetamide The title compound was prepared from 5-bromo-N-[4-methoxy-3-(4-methylpiperazin-1-yl)phenyl]naphth-1-ylacetamide (E20) and 2-methylphenylboronic acid using a similar procedure to Example 4 (48%).

$^1$H NMR (250 MHz, CDCl$_3$) δ(ppm): 8.1 (d, 1H), 7.65–7.25 (m, 9H), 6.9 (m, 3H), 6.7 (d, 1H), 4.2 (s, 2H), 3.8 (s, 3H), 3.05 (br s, 4H), 2.6 (br s, 4H), 2.35 (s, 3H), 2.0 (s, 3H).

EXAMPLE 38

N-[4-Bromo-3-(4-methylpiperazin-1-yl)phenyl]-4-(pyridin-4-yl)naphth-1-ylacetamide The title compound was prepared from 4-(pyridin-4-yl) naphth-1-ylacetic acid (D2) and 4-bromo-3-(4-methylpiperazin-1-yl)aniline (Intermediate 44, EP 0533268A1) using a similar procedure to Example 20 (73%).

$^1$H NMR (250 MHz, CDCl$_3$) δ(ppm): 8.75 (m, 2H), 8.1 (m, 2H), 7.9 (d, 1H), 7.7–7.4 (m, 7H), 7.2 (d, 1H), 6.5 (dd, 1H), 4.3 (s, 2H), 3.2 (m, 4H), 2.5 (m, 4H), 2.3 (s, 3H)

EXAMPLE 39

5-(3,4-Dimethoxyphenyl)-N-4-methoxy-3-(4-methylpiperazin-1-yl)phenyll naphth-1-ylacetamide The title compound was prepared from 5-bromo-N-[4-methoxy-3-(4-methylpiperazin-1-yl)phenyl]naphth-1-ylacetamide (E20) and 3,4-dimethoxyphenylboronic acid using a similar procedure to Example 4 (15%).

$^1$H NMR (250 MHz, CDCl$_3$) δ(ppm): 8.05 (d, 1H), 7.7–7.55 (m, 2H), 7.5–7.3 (m, 3H), 7.2 (d, 1H), 7.1–6.9 (m, 3H), 6.75 (d, 1H), 6.65 (m, 2H), 4.2 (s, 2H), 3.9 (s, 3H), 3.8 (s, 3H), 3.7 (s, 3H), 3.05 (br s, 4H), 2.6 (br s, 4H), 2.3 (s, 3H).

EXAMPLE 40

N-[5-(3-Acetylphenyl)naphth-1-yl]-N'-[4-methoxy-3-(4-methylpiperazin-1-yl)phenyl]urea The title compound was prepared from N-[5-bromonaphth-1-yl]-N'-[3-(4-methylpiperazin-1-yl)phenyl]urea (E19) and 3-acetylphenylboronic acid using a similar procedure to Example 4 (27%).

$^1$H NMR (250 MHz, CDCl$_3$) δ(ppm): 8.1–7.95 (m, 3H), 7.75 (d, 1H), 7.7–7.35 (m, 6H), 7.1 (s, 1H), 7.0–6.9 (m, 2H), 6.8 (m, 2H), 3.85 (s, 3H), 3.1 (br s, 4H), 2.7 (s, 3 H), 2.6 (br s, 4H), 2.35 (s, 3H).

EXAMPLE 41

N-[4-Chloro-3-(1-methylpiperidin-4-yl)phenyl]-4-(pyridin-4-yl)naphth-ylacetamide To a solution of $^4$-(pyridin-4-yl)napth-1-ylacetic acid (D2, 260 mg, 1.0 mmol) in dichloromethane was added 1-hydroxybenzotriazole hydrate (153 mg, 1.0 mmol) and 1-ethyl-3-(3-dimethylaminopropyl)carbodiimide hydrochloride (200 mg, 1.0 mnmol) and the mixture stirred for 0.5 h. To the mixture was added dropwise a solution of 4-chloro-3-(1-methylpiperidin-4-yl)aniline (D7, 200 mg, 0.90 mmol) in dichloromethane (3 ml) and stirring continued for 48 h. Purification of the crude by flash chromatography gave the title compound as a white solid (30 mg, 7%).

$^1$H NMR (250 MHz,CDCl$_3$) δ(ppm): 8.69 (dd, 2H), 8.49 (br s, 1H), 8.13 (d, 1H), 7.83 (d, 1H), 7.47 (m, 5H), 7.41 (dd, 2H), 7.21 (d, 1H), 7.15 (s, 1H), 4.18 (s, 2H), 3.44 (m, 2H), 3.10 (m, 1H), 2.45 (s, 3H), 2.34 (m, 2H), 1.83 (m, 4H).

EXAMPLE 42

5-Bromo-2,3-dihydro-6-(4-methylpiperazin-1-yl)-1-[5-(pyridin-4-yl)naphth-1-ylcarbonl]-1H-indole The title compound was prepared from 5-(pyridin-4-yl) naphth-1-yl carboxylic acid (D8) and 5-bromo-2,3-dihydro-6-(4-methylpiperazin-1-yl)-1H-indole (D13) using a similar procedure to Example 1, obtained as a foam (43%).

$^1$H NMR (250 MHz, CDCl$_3$) δ(ppm): 8.38 (m, 2H), 8.29 (s, 1H), 7.88 (m, 3H), 7.62 (m, 3H), 7.34 (m, 3H), 3.70 (br, 2H), 3.14 (br, 4H), 2.99 (t, 2H), 2.72 (br, 4H), 2.63 (s, 3H).

Pharmacological Data

5-HT$_{1A}$, 5-HT$_{1B}$ and 5-HT$_{1D}$ Receptor Binding

HEK 293 cells expressing 5-HT$_{1A}$ receptors (4×10$^7$/ml) were homogenised in Tris buffer and stored in 1 ml aliquots. CHO cells expressing 5-HT$_{1B}$ receptors (4×10$^7$ cells/ml) were homogenised in Tris buffer and stored in 1.5 ml aliquots. CHO cells expressing 5-HT$_{1D}$ receptors (0.563× 10$^8$/ml) were homogenised in Tris buffer and stored in 1 ml aliquots.

0.4 ml of a cell suspension was incubated with [$^3$H]-5-HT (4nM) for 5-HT$_{1B/1D}$ receptors and [$^3$H]-8-OH DPAT (1nM) for 5-HT$_{1A}$ receptors in Tris Mg HCl buffer (pH 7.7) and test drug, at 37° C. for 45 minutes. Each test drug was tested at 10 concentrations (0.01 mM to 0.3 nM final concentration), with non-specific binding defined using 0.01 mM 5-HT. The total assay volume was 0.5 ml. Incubation was stopped by rapid filtration using a Packard Filtermate (filters pre-soaked in 0.3% polyethylenimine) and radioactivity measured by Topcount scintillation counting. pKi values were calculated from the IC$_{50}$ generated by an iterative least squares curve fitting programme.

Examples 10, 11, 28, 33, 38 and 40 had pKi values >8.0 at 5-HT$_{1A}$, 5-HT$_{1B}$ and 5-HT$_{1D}$ receptors.

What is claimed is:

1. A compound of formula (I) or a salt thereof:

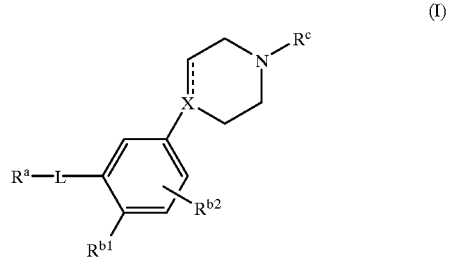

(I)

in which $R^a$ is a group of formula (i)

(i)

is selected from the group consisting of naphthyl, indanyl, tetrahydronaphthyl, 2,3-dihydrobenzofuryl, quinoline, isoquinoline, indole, benzofuran, benzothiazole and benzothiadiazole.

Ris hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, C$_{1-6}$alkanoyl, nitro, trifluoromethyl, cyano, SR$^9$, SOR$^9$, SO$_2$R$^9$, SO$_2$NR$^{10}$R$^{11}$, CO$_2$R$^{10}$, CONR$^{10}$R$^{11}$, CO$_2$NR$^{10}$R$^{11}$, CONR$^{10}$(CH$_2$)$_c$CO$_2$R$^{11}$, (CH$_2$)$_c$NR$^{10}$R$^{11}$, (CH$_2$)$_c$CONR$^{10}$R$^{11}$,(CH$_2$)$_c$NR$^{10}$COR$^{11}$, (CH$_2$)$_c$CO$_2$C$_{1-6}$alkyl, CO$_2$(CH$_2$)$_c$OR$^{10}$, NR$^{10}$R$^{11}$, NR$^{10}$ CO$_2$R$^{11}$, NR$^{10}$CONR $^{10}$R$^{11}$, CR$^{10}$=NOR$^{11}$, CNR$^{10}$=NOR $^{11}$, where R$^9$, R$^{10}$ and R$^{11}$ are independently hydrogen or C$_{1-6}$alkyl and c is 1 to 4;

R$^2$ is hydrogen, halogen, C$_{1-6}$alkyl, C$_{3-6}$cycloalkyl, C$_{3-6}$cycloalkenyl, C$_{1-6}$alkoxy, C$_{1-6}$alkanoyl, phenyl, acyloxy, hydroxy, nitro, trifluoromethyl, cyano, CO$_2$R$^{10}$, CONR$^{10}$R$^{11}$, NR$^{10}$R$^{11}$ I where R$^{10}$ and R$^{11}$ are as defined for R$^1$; a is 1,2or3;

or $R^a$ is a group of formula (ii)

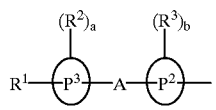

thienyl, furyl, pyrrolyl, triazolyl, imidazolyl, oxazolyl, thiazolyl, oxadiazolyl, isothiazolyl, isoxazolyl, thiadiazolyl, pyrimidyl, pyrazinyl, or a bicyclic heterocyclic group containing 1 to 3 heteroatoms selected from oxygen, nitrogen or sulphur, providing that at least one of $P^2$ and $P^3$ is a bicyclic aryl or bicyclic heterocyclic group;

A is a bond or oxygen, $S(O)_m$ where m is 0 to 2, carbonyl, $CH_2$ or $NR^4$ where $R^4$ is hydrogen or $C_{1-6}$alkyl;

$R^1$ is as defined above for formula (i) or is a 5 to 7-membered heterocyclic ring, containing 1 to 3 heteroatoms selected from oxygen, nitrogen or sulphur, optionally substituted by $C_{1-6}$alkyl, halogen or $C_{1-6}$alkanoyl;

$R^2$ and $R^3$ are independently hydrogen, halogen, $C_{1-6}$alkyl, $C_{3-6}$cycloalkyl, $C_{1-6}$cycloalkenyl, $C_{1-6}$alkoxy, $C_{1-6}$alkanoyl, phenyl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are as defined for $R^1$; and a and b are independently 1, 2 or 3;

L is a group of formula

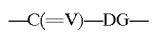

or

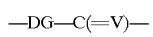

or

V is oxygen or sulphur;

D is nitrogen, carbon or a CH group, G and $G^1$ are each hydrogen or $C_{1-6}$alkyl, providing that D is nitrogen or a CH group, or G together with $R^{b1}$ forms a group W where W is $(CR^{16}R^{17})_t$ where t is 2, 3 or 4 and $R^{16}$ and $R^{17}$ are independently hydrogen or $C_{1-6}$alkyl or W is $(CR^{16}R^{17})_u$-J where u is 0, 1, 2 or 3 and J is oxygen, sulphur, $CR^{16}=CR^{17}$, $CR^{16}=N$, $=CR^{16}O$, $=CR^{16}S$ or $=CR^{16}-NR^{17}$;

Y is —NH— or —$NR^5$— where R5 is $C_{1-6}$ alkyl, or Y is —CH2— or —O—:

X is nitrogen or carbon;

$R^{b1}$ and $R^{b2}$ are independently hydrogen, halogen, hydroxy, $C_{1-6}$alkyl, trifluoromethyl, $C_{1-6}$alkoxy or phenyl, or $R^{b1}$ together with G forms a group W as defined above;

$R^c$ is hydrogen or $C_{1-6}$alkyl; and —is a single bond when X is nitrogen, or a single or double bond when X is carbon.

2. A compound according to claim 1 in which $R^1$ is a halogen atom.

3. A compound according to claim 2 in which $R^2$ and/or $R^3$ are each hydrogen, halogen or a $C_{1-6}$ alkyl group.

4. A compound according to claim 3 in which one of $P^1$, $P^2$ and/or $P^3$ is a naphthyl group.

5. A compound according to claim 4 in which V is oxygen.

6. A compound according to claim 5 in which D is nitrogen and G is hydrogen.

7. A compound according to claim 6 in which $R^{b1}$ and $R^{b2}$ are hydrogen or $C_{1-6}$ alkoxy, or $R^{b1}$ together with G forms a —$(CH_2)_2$— group.

8. A compound according to claim 7 in which X is nitrogen.

9. A compound according to claim 1 which is:
N-[4-methoxy-3-(4-methylpiperazin-1-yl)phenyl]-4-bromonaphth-1-yl carboxamide, 5-bromo-N-[4-methoxy-3-(4-methylpiperazin-1-yl)phenyl]naphth-1-yl carboxamide, N-[4-methoxy-3-(4-methylpiperazin-1-yl)phenyl]quinolin-4-yl carboxamide, N-[4-methoxy-3-(4-methylpiperazin-1-yl)phenyl]-5-(pyridin-4-yl)naphth-1-yl carboxamide, N-[4-methoxy-3-(4-methylpiperazin-1-yl)phenyl]-4-(pyridin-4-yl)naphth-1-yl carboxamide, N-[(4-methoxy-3-(4-methylpiperazin-1-yl)phenyl]-N'-[naphth-1-yl]urea, N-[4-bromonaphth-1-yl]-N'-[(4-methoxy-3-(4-methylpiperazin-1-yl)phenyl]urea, N-[4-methoxy-3-(4-methylpiperazin-1-yl)phenyl]-N'-[4-(pyridin-4-yl)naphth-1-yl]urea, N-[4-methoxy-3-(4-methylpiperizin-1-yl)phenyl]-4-bromonaphth-1-yl acetamide, N-[4-methoxy-3-(4-methylpiperazin-1-yl)phenyl]-4-(pyridin-4-yl)naphth-1-yl acetamide, N-[4-chloro-3-(4-methylpiperazin-1-yl)phenyl]-N'-[4-(pyridin-4-yl)naphth-1-yl]urea, N-[4-methoxy-3-(4-methylpiperazin-1-yl)phenyl]-N'-[naphth-1-yl]thiourea, N-[4-methoxy-3-(1-methylpiperidin-4-yl)phenyl]-N'-[4-(pyridin-4-yl)naphth-1-yl]urea, N-[4-methoxy-3-(4-methylpiperazin-1-yl)phenyl]-N'-[5,6,7,8-tetrahydronaphth-1-yl]urea, N-[indian-5-yl]-N'-[4-methoxy-3-(4-methylpiperazin-1-yl)phenyl]urea, N-[benzo-2, 1,3-thiadiazol-4-yl]-N'-[4-methoxy-3-(4-methylpiperazin-1-yl)phenyl]urea, N-[indol-4-yl]-N'-[4-methoxy-3-(4-methylpiperazin-1-yl)phenyl]urea, N-[4-methoxy-3-(4-methylpiperazin-1-yl)phenyl]-N'-[3,4-methylenedioxyphenyl]urea, N-[5-Bromonaphth-1-yl]-N'-[4-methoxy-3-(4-methylpiperazin-1-yl)phenyl]urea, 5-Bromo-N-[4-methoxy-3-(4-methylpiperazin-1-yl)phenyl]naphth-1-ylacetamide, N-[4-Methoxy-3-(4-methylpiperazin-1-yl)phenyl]-N'-[2-methylquinolin-6-yl]urea, N-[Isoquinolin-5-yl]-N'-[4-methoxy-3-(4-methylpiperazin-1-yl)phenyl]urea, N-[Benzothiazol-6-yl]-N'-[4-methoxy-3-($^4$-methylpiperazin-1-yl)phenyl]urea, N-[4-Methoxy-3-(4-methylpiperazin-1-yl)phenyl]-N-[quinolin-3-yl]urea, N-[4-Methoxy-3-(4-methylpiperazin-1-yl)phenyl]-N'-[quinolin-6-yl]urea, N-[4-Methoxy-3-(4-methylpiperazin-1-yl)phenyl]-N'-[quinolin-5-yl]urea, N-[2,3-Dihydrobenzofuran-5-yl]-N'-[4-methoxy-3-(4-methylpiperazin-1-yl)phenyl]urea, N-[4-Methoxy-3-(4-methylpiperazin-1-yl)phenyl]-4-pyridin-3-yl)naphth-1-yacetamide, N-[4-Methoxy-3-(4-methylpiperazin-1-yl)phenyl]-N'[5-(pyridin-3-yl)naphth-1-yl]urea, 4-(4-Acetylphenyl)-N-[4-methoxy-3-(4-methylpiperazin-1-yl)phenyl]naphth-1-ylacetamide, 4-(3-Acetylphenyl)-N-[4-methoxy-3-(4-methylpiperazin-1-yl)phenyl]naphth-1-ylacetarnide, 5-(3-Acetylphenyl)-N-[4-methoxy-3-(4-methylpiperazin-1-yl)phenyl]naphth-1-ylacetamide, N-[4-Methoxy-3-(4-methylpiperazin-1-yl)phenyl]-N'-[5-phenylnaphth-1-yl]urea, N-[4-Methoxy-3-(4-methylpiperazin-1-yl)phenyl]-5-(pyridin-3-yl)naphth-1-ylacetamide, N-[4-Methoxy-3-(4-methylpiperazin-1-yl)phenyl]-5-phenylnaphth-1-ylacetamide, 5-(4-Acetylphenyl)-N-[4-methoxy-3-(4-methylpiperazin-1- yl)phenyl]naphth-1-ylacetamide, N-[4-Methoxy-3-(4-methylpiperazin-1-yl)phenyl]-5-(2-methylphenyl)naphth-1-ylacetamide, N-[4-Bromo-3-(4-methylpiperazin-1-yl)phenyl]-4-(pyridin-4-yl)naphth-1-ylacetamide, 5-(3,4-Dimethoxyphenyl)-N-[4-methoxy-3-(4-methylpiperazin-1-yl)phenyl]naphth-1-ylacetamide, N-[5-(3-Acetylphenyl)naphth-1-yl]-N'-[4-methoxy-3-(4-methylpiperazin-1-yl)phenyl]urea, N-[4-Chloro-3-(1-methylpiperidin-4-yl)phenyl]-4-(pyridin-4-yl)naphth-1-ylacetamide, 5-Bromo-6-(4-methylpiperazin-1-yl)-1-[5-(pyridin-4-yl)naphth-1ylcarbonyl]-1H-indol or pharmaceutically acceptable salts thereof.

10. A process for the preparation of a compound of formula (I) according to claim 1 or a pharmaceutically acceptable salt thereof which comprises (a) where L is —C(=V)—DG— or —DG—C(=V)—, coupling a compound of formula (II):

Ra—L¹  (II)

with a compound of formula (III).

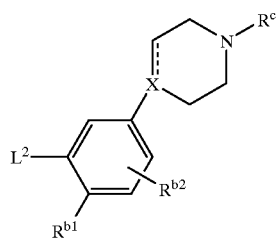

(III)

in which $R^a, R^{b1}, R^{b2}$, $R^c$ and X are as defined in formula (I) and $L^1$ and $L^2$ contain the appropriate functional groups which are capable of reacting together to form the L moiety; or (b) where L is —Y—C(=V)—DG¹ in which D is nitrogen and Y is NH, coupling a compound of formula (IV):

$R^a$ —NC(=V)  (IV)

in which $R^a$ and V are as defined in formula (I) or a protected derivative thereof with a compound of formula (V):

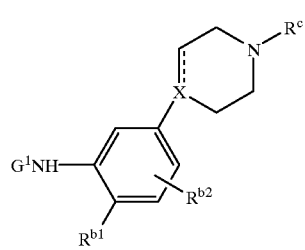

(V)

in which $R^{b1}$, $R^{b2}$, $R^c$, $G^1$ and X are as defined in formula (I), or a protected derivative thereof; or (c) where L is —Y—C(=V)—DG¹ — in which D is nitrogen and and Y is NH or NR⁵, reacting a compound of formula (VI)

$R^a$ —NH₂ or $R^a$ —NR⁵H  (VI)

in which $R^a$ and $R^5$ are as defined in formula (I) with a compound of formula (V) together with an appropriate urea forming agent;

(d) where L is —Y—C(=V)—DG¹ — in which D is nitrogen and Y is CH₂ or O, reacting a compound of formula (VII)

$R^a$ —Y—(C=O)—L³  (VII)

in which $R^a$ is as defined in formula (I), and $L^3$ is an appropriate leaving group, with a compound of formula (V)

(e) where D is CH, reacting a compound of formula (VI)

$R^a$ —NH₂  (VI)

in which $R^a$ is as defined in formula (I) with a compound of formula (VII)

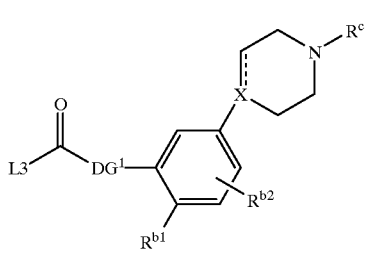

(VII)

in which D is CH, and $G^1$, X, $R^{b1}$, $R^{b2}$ and $R^c$ are as defined in formula (I) and $L^3$ is an appropriate leaving atom and optionally thereafter:
removing any protecting groups,
converting a compound of formula (I) into another compound of formula (I),
forming a pharmaceutically acceptable salt.

11. A pharmaceutical composition which comprises a compound according to claim 1 and a pharmaceutically acceptable carrier.

12. A method of treating a CNS disorder selected from the group consisting of:
mood disorders, depression, seasonal affective disorder, dysthmia, anxiety disorders, generalized anxiety, panic disorder, agoraphobia, social phobia, obsessive compulsive disorder, post-traumatic stress disorder, memory disorders, dementia, amnestic disorders, age associated memory impairment, eating behavior disorders, anorexia nervosa, bulimia nervosa, Parkinson's disease, dementia associated with Parkinson's disease, neuroleptic-induced Parkinsonism, tardive dyskinesias and psychiatric disorders;
by administering to a subject in need of treatment a safe and pharmaceutically effective amount of a compound according to claim 1.

13. A method according to claim 12 wherein the disorder is anxiety or depression.

* * * * *